(12) United States Patent
Zuckermann et al.

(10) Patent No.: US 7,422,861 B2
(45) Date of Patent: Sep. 9, 2008

(54) OLIGONUCLEOTIDE TRANSFECTION SCREENING METHOD

(75) Inventors: Ronald N. Zuckermann, El Cerrito, CA (US); Christoph J. Reinhard, Alameda, CA (US); Anne B Jefferson, Oakland, CA (US); Eric Beausoleil, Clamart (FR)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 74 days.

(21) Appl. No.: 10/025,423

(22) Filed: Dec. 18, 2001

(65) Prior Publication Data

US 2002/0151062 A1 Oct. 17, 2002

Related U.S. Application Data

(60) Provisional application No. 60/329,185, filed on Oct. 11, 2001, provisional application No. 60/257,975, filed on Dec. 23, 2000.

(51) Int. Cl.
*G01N 33/53* (2006.01)
*C12P 21/02* (2006.01)

(52) U.S. Cl. .............................. 435/7.2; 435/6; 435/4; 435/455; 435/459

(58) Field of Classification Search ................. 435/7.1, 435/6, 4, 455, 458, 7.2, 459; 514/44
See application file for complete search history.

(56) References Cited

U.S. PATENT DOCUMENTS

| | | | |
|---|---|---|---|
| 5,481,020 A | 1/1996 | Ng et al. | |
| 5,877,278 A | 3/1999 | Zuckermann et al. | |
| 5,935,936 A * | 8/1999 | Fasbender et al. | 514/44 |
| 6,153,596 A * | 11/2000 | Liotta et al. | 514/44 |
| 6,468,986 B1 | 10/2002 | Zuckermann et al. | |

FOREIGN PATENT DOCUMENTS

| | | |
|---|---|---|
| EP | 0 639 584 | 2/1995 |
| GB | 2295152 | 5/1996 |
| WO | WO91/19735 | 12/1991 |
| WO | WO 92/00091 A | 1/1992 |
| WO | WO92/04320 | 3/1992 |
| WO | WO 94/02515 A | 2/1994 |
| WO | WO94/06451 | 3/1994 |
| WO | WO94/13623 | 6/1994 |
| WO | WO96/40201 | 12/1996 |
| WO | WO 98/06437 A | 2/1998 |
| WO | WO 98/08092 A | 2/1998 |
| WO | WO98/10857 | 3/1998 |
| WO | WO98/17384 | 4/1998 |
| WO | WO98/49187 | 11/1998 |
| WO | WO 99/08711 A1 | 2/1999 |
| WO | WO 99/58476 | 11/1999 |
| WO | WO 01/16306 | 3/2001 |

OTHER PUBLICATIONS

Lam et al, Chem. Rev. 1997, 97, 411-448.*
Furka et al Int. J. Peptide Protein Res. 37, 1991, 487-493.*
Murphy, John E., et al., "A combinatorial approach to the discovery of efficient cationic peptoid reagents for gene delivery", *Proc. Natl. Acad. Sci. USA* 95:1517-1522, Feb. 1998.
Byk, Gerardo, et al., "Synthesis, Activity, and Structure—Activity Relationship Studies of Novel Cationic Lipids for DNA Transfer", *J. Med. Chem*: 41:224-235, 1998.
van de Wetering, Petra, et al., "Structure—Activity Relationships of Water-Soluble Cationic Methacrylate/Methacrylamide Polymers for Nonviral Gene Delivery", *Bioconjugate Chem* 10:589-597, 1999.
Gonzalez, Jesus E., et al., "Intracellular detection assays for high-throughput screening", *Current Opinion in Biotechnology* 9:624-631, 1998.
Silverman, Lauren, et al., "New assay technologies for high-throughput screening", *Current Opinion in Chemical Biology* 2:397-403, 1998.
Sittampalem, G. Sitta, et al., "High-throughput screening: advances in assay technologies", *Current Opinion in Chemical Biology* 1:384-391, 1997.
Kang et al., "Delivery of Antisense Oligonucleotides and Plasmid DNA with Various Carrier Agents", *Antisense & Nucleic Acid Drug Debelopment*, 9:497-505, 1999.
Lebl et al., "Multiple release of equimolar amounts of peptides from a polymeric carrier using orthogonal linkage-cleavage chemistry," *Int. J. Peptide Protein Res.* 41:201-203, (1993).
International Search Report for PCT/US01/49175.
Benimetskaya, et al., "Cationic porphyrins: novel delivery vehicles for antisense oligodeoxynucleotides" Nucleic Acids Research, 1998, vol. 26, No. 23.
Bennett, et al., "Cationic Lipids Enhance Cellular Uptake and Activity of Phosphorothioate Antisense Oligonucleotides" Molecular Pharmacology 41:1023-1033 Oct. 1991.

(Continued)

*Primary Examiner*—T. D. Wessendorf
(74) *Attorney, Agent, or Firm*—Mark Seka; Anna Gavrilova

(57) ABSTRACT

Different-sequence peptoids, including lipid- and sterol-conjugated peptoids, are found to be effective in transfection of cells with oligonucleotides. Combinatorial libraries of such peptoids can be screened efficiently in a high-throughput format, and selected peptoids are identified post-screening.

10 Claims, 9 Drawing Sheets

OTHER PUBLICATIONS

Cao, et al., "Delivery and Pathway in MCF7 Cells of DNA Vectorized by Cationic Liposomes Derived from Cholesterol" Antisense & Nucleic Acid Drug Development 10:369-380 (2000).

Carr, et al. "Integration of Mass Spectrometry in Analytical Biotechnology" Anal. Chem. 1991, 63, 2802-2824.

RK Delong, "Novel Cationic amphiphiles as delivery agents for antisense oligonucleotides" Nucleic Acids Research, 1999, vol. 27, No. 16, 3334-3341.

Felgner, et al. "Lipfection: A highly efficient, lipid-mediated DNA-transfection procedure" Proc. Natl. Acad. Sci USA vol. 84, pp. 7413-7417 Nov. 1987.

Figliozzi, et al. "Synthesis of N-Substituted Glycine Peptiod Libraries" Methods in Enzymology, vol. 267.

Garcia-Chaumont, et al. "Delivery systems for antisense oligonucleotides" Pharmacology & Therapeutics 87 (2000) 255-277.

Huang, et al. "Liptiods—novel cationic lipids for cellular delivery of plasmid DNA in vitro" Chemistry & Biology Jun. 1998 5:345-354.

Lam, et al. "A new type of synthetic peptide library for identifying ligand-binding activity" Nature vol. 354, Nov. 1991.

Lewis, et al. "A serum-resistant cytofectin for cellular delivery of antisense oligodeoxyncleotides and plasmid DNA" Proc Natl. Acad. Sci. USA vol. 93, pp. 3176-3181, Apr. 1996 Biochemistry.

Marcusson, et al. "Phosphorothioate oligodeoxyribonucleotides dissociate from cationic lipids before entering the nucleus" Nucleic Acids Research, 1998 vol. 26, No. 8 2016-2023.

Morris, et al. "A new peptide vector for efficient delivery of oligonucleotides into mammalian cells" Nucleic Acids Research, 1997, vol. 25, No. 14 2730-2736.

Smith, et al. "New Developments in Biochemcial Mass Spectrometry: Electrospray Ionization" Anal. Chem. 1990, 62, 882-899.

Terrett, et al. "Combinatorial Synthesis—The Design of Compound Libraries and their Application to Drug Discovery" Tetrahedron Report No. 377 vol. 51, No. 30, pp. 8135-8173, 1995.

Thompson, et al. "Synthesis and Application of Small Molecule Libraries" Chem. Rev. 1996, 96, 555-600.

Yoo, et al. "Enhanced delivery of antisense oligonucleotides with fluorophore-conjugated PAMAM dendrimers" Nucleic Acids Research, 2000 vol. 28, No. 21 4225-4231.

Zuckermann, et al. Efficient Method for the Preparation of Peptides [Oligo (N-susbtituted glycines)] by Submonomer Solid-Phase Synthesis, J. Am. Chem. Soc. 1992, 114, 10646-10657.

Zuckermann, et al. "Automated Peptide-Resin Deprotection/Cleavage by a Robotic Workstation", Peptide Research, vol. 5, No. 3 (1992).

Bunin, Barry A., "The Combinatorial Index", San Diego: Academic Press c 1998 322 pages.

* cited by examiner

DMPE(NaeNmpeNmpe)₃

Chol-ß-ala-(NaeNmpeNmpe)₃

OLIGONUCLEOTIDE TRANSFECTION SCREENING METHOD

This application claims priority to U.S. provisional application Ser. No. 60/257,975, filed on Dec. 23, 2000, and U.S. provisional application Ser. No. 60/329,185 filed on Oct. 11, 2001, both of which are hereby incorporated by reference in their entirety.

FIELD OF THE INVENTION

The present invention relates to methods for screening different-sequence peptoids, including lipid- and sterol-conjugated peptoids, particularly combinatorial libraries of such compounds, for effectiveness in transfection of cells with oligonucleotides.

REFERENCES

Bartlett, P. A., Santi, D. V. et al., "Preparation of modified peptides with protease resistance." PCT Pubn. No. WO 91/19735 (1991).

Benimetskaya, L. et al., "Cationic porphyrins: novel delivery vehicles for antisense oligodeoxynucleotides. *Nucleic Acids Res* 26(23): 5310-7 (1998).

Bennett, C. F. et al., "Cationic lipids enhance cellular uptake and activity of phosphorothioate antisense oligonucleotides. *Mol Pharmacol* 41(6): 1023-33 (1992).

Bunin, B., "Combinatorial Index," Acad. Press (1998).

Byk et al., *J Med Chem* 41:224 (1998).

Cao, A. et al., "Delivery and pathway in MCF7 cells of DNA vectorized by cationic liposomes derived from cholesterol." *Antisense Nucleic Acid Drug Dev* 10(5): 369-80 (2000).

Carr, S. A. et al., "Integration of mass spectrometry in analytical biotechnology." *Anal Chem* 63(24): 2802-24 (1991).

DeLong, R. K. et al., "Novel cationic amphiphiles as delivery agents for antisense oligonucleotides." *Nucleic Acids Res* 27(16): 3334-41 (1999).

Desai, M. C., Nuss, J. M. et al., "Combinatorial libraries of substrate-bound cyclic organic compounds." PCT Publication. No. WO 96/40201 (1996).

Felgner et al., *Proc. Natl. Acad. Sci. USA* 84:7413 (1987).

Figliozzi, G. M. et al., "Synthesis of N-substituted glycine peptoid libraries." *Methods Enzymol* 267: 437-47 (1996).

Furka, A. et al., "General method for rapid synthesis of multicomponent peptide mixtures." *Int J Pept Protein Res* 37(6): 487-93 (1991).

Garcia-Chaumont, C. et al., "Delivery systems for antisense oligonucleotides." *Pharmacol Ther.* 87(2-3): 255-77 (2000).

Hadas, E. and Hornik, V., "Preparation and screening of highly diverse peptide libraries for binding activity." EP 0639584 (1995).

Haenel, J., "Method for multiple solid phase synthesis." DE 4403967 (1994).

Horwell, D. C., Pritchard, M. C. et al., "Preparation of N-substituted cycloalkyl and polycycloalkyl α-substituted tryptophan derivatives as cholecystokinin antagonists." PCT Pubn. No. WO 92/04320 (1992).

Huang, C. Y. et al., "Lipitoids—novel cationic lipids for cellular delivery of plasmid DNA in vitro". *Chem Biol* 5(6): 345-54 (1998).

Kang, S. H., E. L. Zirbes, and R. Kole, Delivery of antisense oligonucleotides and plasmid DNA with various carrier agents". *Antisense Nucleic Acid Drug Dev* 9(6): 497-505 (1999).

Kobylecki, R. J. and Gardner, J. M. F., "Preparation of a library of compounds by solid-phase synthesis." GB 2295152 (1996).

Lam, K. S. et al., "A new type of synthetic peptide library for identifying ligand-binding activity." *Nature* 354(6348): 82-4 (1991).

Laser & Medizin Technologie GMBH, "Apparatus for solid-phase synthesis of peptide combinatorial libraries and fluorescent determination of coupling-reaction completion." DE 20005738 (2000).

Lewis, J. G. et al., "A serum-resistant cytofectin for cellular delivery of antisense oligodeoxynucleotides and plasmid DNA." *Proc Natl Acad Sci USA* 93(8): 3176-81 (1996).

Marcusson, E. G. et al., "Phosphorothioate oligodeoxyribonucleotides dissociate from cationic lipids before entering the nucleus." *Nucleic Acids Res* 26(8): 2016-23 (1998).

Morris, M. C. et al., "A new peptide vector for efficient delivery of oligonucleotides into mammalian cells. *Nucleic Acids Res* 25(14): 2730-6 (1997).

Murphy, J. E. et al., "A combinatorial approach to the discovery of efficient cationic peptoid reagents for gene delivery. *Proc Natl Acad Sci USA* 95(4): 1517-22 (1998).

Ng, S., Warne, R. L. et al., "Peptoids as opioid receptor ligands." U.S. Pat. No. 5,481,020 (1996).

Smith, R. D. et al., "New developments in biochemical mass spectrometry:electrospray ionization. *Anal Chem* 62(9): 882-99 (1990).

Terrett et al., "Combinatorial Synthesis: The Design of Compound Libraries and Their Application to Drug Discovery," *Tetrahedron* 51(30):8135-8173 (1995).

Thompson et al., "Synthesis and Applications of Small Molecule Libraries," *Chem. Rev.* 96:55-600 (1996).

van de Wetering et al., *Bioconj Chem* 10:589 (1999).

Yoo, H. and R. L. Juliano, Enhanced delivery of antisense oligonucleotides with fluorophore-conjugated PAMAM dendrimers." *Nucleic Acids Res* 28(21): 4225-31 (2000).

Zuckermann, R. N. and S. C. Banville, Automated peptide-resin deprotection/cleavage by a robotic workstation. *Pept Res* 5(3): 169-74 (1992).

Zuckermann, R. N., Chinn, J. P. et al., "Inverse filtration apparatus and its use." PCT Pubn. No. WO 98/17384 (1998).

Zuckermann, R. N., Dubois-Stringfellow, N. et al., "Compositions and methods for polynucleotide delivery." PCT Pubn. No. WO 98/06437 (1998).

Zuckermann, R. N., Goff, D. A. et al., "Solid-phase synthesis of N-substituted glycine peptide combinatorial libraries and nitrogen heterocycle combinatorial libraries." U.S. Pat. No. 5,877,278 (1999).

Zuckermann, R. N., Huang, C. et al., "Lipid-polyamide conjugates and compositions for nucleic acid delivery." PCT Pubn. No. WO 99/08711 (1999).

Zuckermann, R. N., Kerr, J. M. et al., "Synthesis of N-substituted oligomers (polyglycines)". PCT Pubn. No. WO 94/06451 (1994).

Zuckermann, R. N., Kerr, J. M. et al., *J Am Chem Soc* 114:10646-47 (1992).

Zuckermann, R. N., Siegmund, A. C. et al., "Apparatuses for solid-phase chemical synthesis involving arrays of modular reaction vessels." PCT Pubn. No. WO 98/10857 (1998).

Zuckermann, R. N., Troung, K. et al., "Apparatus for synthesis of oligomers, especially peptoids, with reagent recycling". PCT Pubn. No. WO 98/49187 (1998).

BACKGROUND OF THE INVENTION

With the recent explosion in gene identification, it has become crucial to develop efficient tools for functional genomics. One of the most valuable is the use of antisense oligonucleotide technology to validate gene function in cell-based assays. The ability of antisense oligonucleotides to decrease cellular message levels is now well established. However, their efficacy depends, in part, on the cellular concentration achieved and on the location of the oligonucleotides within the cell (Garcia-Chaumont, 2000; Marcusson, 1998). Many agents have been developed for delivery of DNA, and several of these have been shown to deliver nucleic acids into cells in vitro. These agents include cationic polymers, such as polylysine, and cationic lipids. For example, the liposomal composition Lipofectin® (Felgner et al., 1987), containing the cationic lipid DOTMA (N-[1-(2,3-dioleyloxy) propyl]-N,N,N-trimethylammonium chloride) and the neutral phospholipid DOPE (dioleyl phosphatidyl ethanolamine), is widely used. See also Benimetskaya, 1998; Bennett, 1992; Cao, 2000; DeLong, 1999; Kang, 1999; Morris, 1997; Lewis, 1996; and Yoo, 2000.

However, little attention has been placed on the development of carriers optimized for oligonucleotides. This point is especially important since antisense oligonucleotides have become an integral part of functional genomics and target validation in drug discovery. Ideally, transfection agents should be easy to use and give reproducible, efficient transfection of oligonucleotides into cells with minimal interference with biological systems. Unfortunately, many known transfection agents suffer from problems such as poor functional delivery, cellular toxicity, or incompatibility with serum in the transfection medium.

Toxicity and/or inefficient delivery by such vehicles in a growing number of cell lines requires that new candidate delivery vehicles be prepared and tested for their activity, both in general and for cell specific delivery. However, polycationic carriers such as those known in the art typically must be synthesized, purified, and tested individually, and many cationic lipids require formulation with DOPE for optimal activity. Accordingly, they are not amenable to structural variation by combinatorial synthesis or to high throughput screening. To date, screening of such compounds has been carried out on limited numbers of known, preselected compositions. See, for example, Byk et al., 1998; van de Wetering et al., 1999. Accordingly, there is a need for more efficient, high throughput synthesis and screening of candidate transfection agents.

Lipid-cationic peptoid conjugates, referred to as "lipitoids" and "cholesteroids", have been shown to be effective reagents for the delivery of plasmid DNA to cells in vitro. These agents are able to condense plasmid DNA into small particles, protect it from nuclease degradation, and efficiently mediate the transfection of several cell lines (Murphy, 1998). See, for example, co-owned PCT publications WO 98/06437 and WO 99/08711 (Zuckermann et al.), corresponding to co-owned U.S. applications Ser. Nos.08/910,647 and 09/132, 808, which are hereby incorporated by reference. Complexing of lipid-peptoid conjugates with plasmid DNA is described in Huang et al., 1998. Such compounds have also been shown to efficiently deliver oligonucleotides (i.e., shorter-length DNA or DNA analogs) into a variety of primary and tumor cell lines, as described in co-owned and co-pending U.S. application Ser. No.09/648,254. This is in contrast to many commercially available transfecting agents, which are less effective in delivery of oligonucleotides than in delivery of plasmid DNA. The lipid-peptoid conjugates can be synthesized by automated synthesis on solid phase and do not need to be formulated with other lipids before use. Accordingly, such compounds are well suited for combinatorial synthesis and high throughput screening, as further described herein.

SUMMARY OF THE INVENTION

In one aspect, the invention provides a method for screening a peptoid, e.g. a lipitoid or a cholesteroid, for effectiveness in transfecting a cell with an oligonucleotide. The method includes the steps of: providing a plurality of different-sequence peptoids in separated compartments; forming a peptoid-oligonucleotide mixture in at least one of these compartments; contacting this mixture with a cell; and determining the degree of transfection of the cell by the oligonucleotide. The degree of transfection may be determined by, for example, employing an oligonucleotide which is an antisense oligonucleotide directed against an expressed sequence in said cell, and detecting an alteration in the level of said sequence in said cell. The peptoid may then be identified, particularly if it is a transfecting peptoid. Non-transfecting peptoids may also be identified.

In one embodiment, the peptoids are supported on solid particles; preferably, each compartment contains a single particle, and each particle contains a single peptoid; that is, the peptoids bound thereto have the same sequence. The method then includes the further step of releasing the peptoid from the particle, prior to formation of the at least one peptoid-oligonucleotide mixture.

In selected embodiments, the different-sequence peptoids have the general formula I:

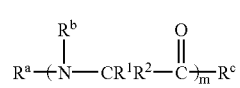

I where
$R^a$ is selected from the group consisting of alkyl, aryl, aralkyl, aralkenyl, and aralkynyl, any of which may be substituted with one or more groups X; hydrogen, —OH, —SH, —COOH, sulfonyl, and a lipid moiety, wherein the lipid moiety may be conjugated to a linker moiety, each $R^b$ is independently selected from the group consisting of alkyl, aryl, aralkyl, aralkenyl, and aralkynyl, any of which may be substituted with one or more groups X; and hydrogen, wherein at least one group $R^b$ is not hydrogen;

$R^c$ is selected from the group consisting of alkyl, aryl, aralkyl, aralkenyl, and aralkynyl, any of which may be substituted one or more groups X; hydrogen, —OH, —SH, —NH$_2$, —NHR, —NH(C=O)R, where R is lower alkyl; sulfonyl, hydrazine, and a lipid moiety, wherein the lipid moiety may be conjugated to a linker moiety;

$R^1$ and $R^2$ are independently selected from hydrogen, lower alkyl, and lower alkoxy;

X is selected from hydroxy, alkoxy, amino, guanidino, amidino, alkylamino, alkylthio, halogen, nitro, cyano, keto, aldehyde, carboxylic acid, carboxylic ester, carboxylic amide, sulfonic acid and sulfonic ester; and m is an integer selected from 2 to about 50.

In further selected embodiments, $R^a$ comprises a lipid moiety, and $R^c$ is selected from —NH$_2$, —NHR, and —NH(C=O)R, where R is lower alkyl. In one embodiment, the lipid moiety is a sterol. Formula I includes poly(N-substituted) glycines, i.e. where each of $R^1$ and $R^2$ is hydrogen.

In preferred embodiments, at least one $R^b$ includes a group which is cationic at physiologically relevant pH, and at least one $R^b$ is uncharged at physiologically relevant pH. The cationic group may be selected from, for example, aminoalkyl, ammonium, such as quaternary alkyl ammonium, guanidino, amidino, imidazolium, pyridinium, and cationic sidechains found on naturally occurring amino acids. The uncharged group may be selected from, for example, aralkyl, such as benzyl or phenethyl, which may be methoxy-substituted, and neutral sidechains found on naturally occurring amino acids.

The present invention also provides, in a related aspect, a method for efficiently screening a library of different-sequence peptoids for effectiveness in transfecting a cell with an oligonucleotide. The method comprises the steps of:

(i) contacting each member of such a library with an oligonucleotide, to form a plurality of peptoid-oligonucleotide mixtures, (ii) contacting each mixture with a cell;

(iii) screening each cell for transfection of the oligonucleotide; and (iv) identifying transfecting peptoids in mixtures contacted with transfected cells.

The library of peptoids is most conveniently provided in an array of physically separated compartments. Typically, the peptoids are supported on solid particles. In this case, the peptoids are released from the particles prior to the contacting step (i). In preferred embodiments, each compartment contains a single particle, and each particle contains a single peptoid.

Screening may comprise detecting a label on the oligonucleotide in transfected cells, or, when the oligonucleotide is an antisense oligonucleotide directed against an expressed sequence in the cell, detecting an alteration in the level of that sequence in the cell.

A duplicate array of the plurality of peptoids may be created, prior to contacting with oligonucleotide, which is useful for later identification purposes. Typically, this step follows release of peptoids from solid supports. Following screening, peptoids in the duplicate array located at positions corresponding to transfecting peptoids, identified by screening, are characterized using appropriate methods and materials, e.g. by mass spectrometry, for example, by tandem mass spectrometry (MS-MS).

In other embodiments of these methods, the cells comprise distinct cell types, and the identifying is effective to identify peptoids capable of selectively delivering oligonucleotides to a selected cell type (e.g. a tumor cell, or an endothelial cell) relative to a non-selected cell type (a non-tumor cell or an epithelial cell, respectively).

It will be appreciated that the methods of the invention allow identification of effective peptoids after screening, and does not require that the sequences of the peptoids, e.g. peptoids in a combinatorial library, be known beforehand. The peptoids described herein, which include lipitoids and cholesteroids, present the advantages of being good candidates for efficient transport of oligonucleotides, and being amenable to combinatorial synthesis and high throughput screening.

Also provided is a method of determining the sequence of an analyte peptoid by tandem mass spectrometry, where the N-substituents on the peptoid are selected from a known population of substituents. The method comprises (a) determining predicted molecular weights of fragments that would be produced by cleaving amide bonds in at least one theoretical peptoid, having a sequence based on one combination of the above-referenced known population of N-substituents; (b) subjecting the analyte peptoid to MS-MS fragmentation, to produce a population of analyte fragment ions of various molecular weights; and (c) determining whether the molecular weights of said analyte fragments correspond to the predicted molecular weights, and thus whether the analyte peptoid has the sequence of the theoretical peptoid of (b). Preferably, predicted molecular weights of fragments are determined for a plurality of theoretical peptoids, having sequences based on different combinations of the above-referenced known population of N-substituents. In one embodiment, the N-substituents at one or more selected positions in the analyte peptoid are predetermined.

These and other objects and features of the invention will become more fully apparent when the following detailed description of the invention is read in conjunction with the accompanying drawings.

DETAILED DESCRIPTION OF THE INVENTION

I. Definitions

Figure 1A:
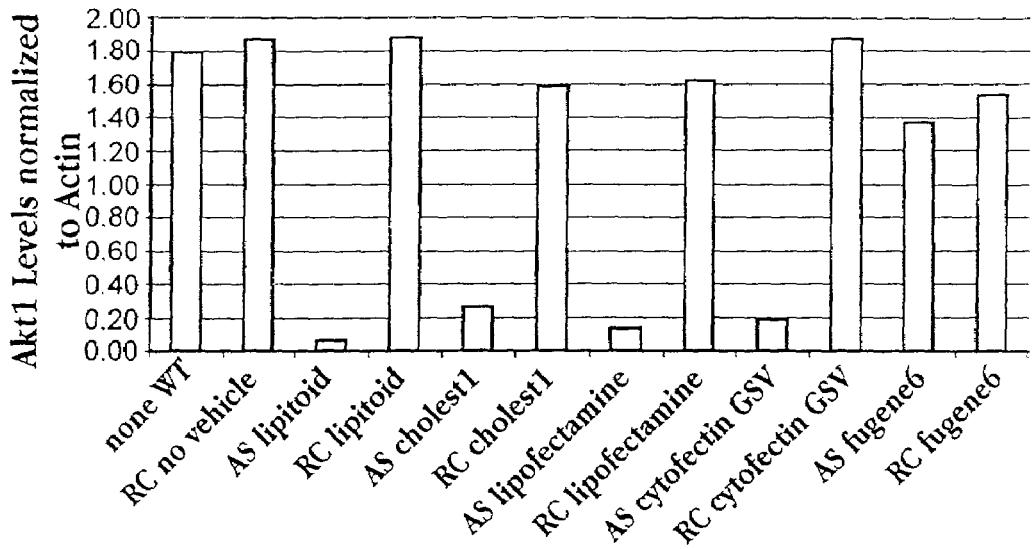
FIGS. 1A-B compare transfection efficiency (1A) and toxicity (1B) of peptoid transfection agents (Lipitoid 1 and Cholesteroid 1; structures shown in FIGS. 1C-D, respectively) with that of commercially available transfection agents Lipofectamine®, Cytofectin™ GSV, and FuGene™ 6 in transfection of SKOV3 cells with Akt1 antisense (AS) and/or reverse control (RC) oligonucleotides.

The terms below have the following meanings unless indicated otherwise.

A "combinatorial library", in general, is a collection of compounds based upon a core structure which has independently variable substituents, functional groups or other structural elements. For the range of chemical moieties selected for each of the independently variable elements, compounds containing all possible permutations of those elements may be present in the library. The method for preparing a combinatorial library is preferably such that all or any combination of diverse members of the library can be synthesized simultaneously.

The peptoid libraries discussed herein typically contain 2 to about 1000, preferably about 10 to 500, and most preferably about 10 to 100 different-sequence peptoids.

A "plurality" of members of a library or array includes all or any two or more members of the library or array, and typically includes at least half of the array.

The terms "solid phase", "resin", "bead" and "particle" refer to any solid support or substrate on which the reaction steps of chemical syntheses involving a sequence of reaction steps can be carried out. Thus, the term includes particulate substrates such as polystyrene resins which have traditionally been employed in standard Fmoc chemical syntheses, such as "Rink amide" resin from Nova Biochem.

A "peptoid" is a poly(N-substituted amide), preferably a poly(N-substituted glycine), as described, for example, in PCT Publications WO 94/06451, WO 98/06437, WO 99/08711, and U.S. Pat. No. 5,877,278 (Zuckermann et al.). For preparation of peptoids, see these references as well as: Bartlett, Santi et al. 1991; Horwell, Pritchard et al. 1992; Haenel 1994; Zuckermann and Kerr 1994; Hadas and Hornik 1995; Desai, Nuss et al. 1996; Kobylecki and Gardner 1996; Ng, Warne et al. 1996; Zuckermann, Siegmund et al. 1998; Zuckermann, Troung et al. 1998; Zuckermann, Chinn et al. 1998; Zuckermann, Goffet al. 1999; 2000; and DE Utility Model Pubn. No. 20005738, all cited above, each of which is incorporated herein by reference in its entirety and for all purposes.

One class of peptoids has the general formula I:

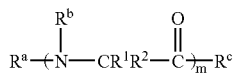

I where $R^a$ is selected from the group consisting of alkyl, aryl, aralkyl, aralkenyl, and aralkynyl, any of which may be substituted with one or more groups X; hydrogen, —OH, —SH, —COOH, sulfonyl, and a lipid moiety, wherein the lipid moiety may be conjugated to a linker moiety, each $R^b$ is independently selected from the group consisting of alkyl, aryl, aralkyl, aralkenyl, and aralkynyl, any of which may be substituted with one or more groups X; and hydrogen, where at least one group $R^b$ is not hydrogen;

$R^c$ is selected from the group consisting of alkyl, aryl, aralkyl, aralkenyl, and aralkynyl, any of which may be substituted one or more groups X; hydrogen, —OH, —SH, —NH$_2$, —NHR, —NH(C=)R, where R is lower alkyl; sulfonyl, hydrazine, and a lipid moiety, wherein the lipid moiety may be conjugated to a linker moiety;

$R^1$ and $R^2$ are independently selected from hydrogen, lower alkyl, and lower alkoxy;

X is selected from hydroxy, alkoxy, amino, guanidino, amidino, alkylamino, alkylthio, halogen, nitro, cyano, keto, aldehyde, carboxylic acid, carboxylic ester, carboxylic amide, sulfonic acid and sulfonic ester; and m is an integer selected from 2 to about 50.

In selected embodiments, $R^c$ is selected from —NH$_2$, —NHR, and —NH(C=O)R, where R is lower alkyl. Where each of $R^1$ and $R^2$ is hydrogen, the molecule is a poly(N-substituted glycine). With respect to the peptoid N-side chains, in selected embodiments, at least one $R^b$ includes a group which is cationic at physiologically relevant pH (e.g. aminoalkyl, quaternary ammonium, guanidino, amidino, imidazolium, pyridinium), and at least one $R^b$ is uncharged at physiologically relevant pH. Examples include alkyl and aralkyl; specific examples are isopropyl and (p-methoxyphenyl) ethyl. Cationic or neutral side chains of naturally occurring acids may also be used. Preferably, each group $R^b$ includes either a cationic or uncharged group. A particularly preferred structure includes a repeating sequence of one cationic group and two uncharged groups at $R^b$.

A "lipid moiety" is a hydrophobic moiety having a substantial hydrocarbon component, preferably comprising a group selected from $C_{10}$-$C_{50}$ branched or unbranched alkyl, alkenyl or alkynyl, $C_{14}$-$C_{50}$ aryl, aralkyl, aralkenyl, or aralkynyl, or a steroid nucleus. Examples of lipid moieties include dialkyl- or dialkenyl-phospholipids, such as phosphatidyl cholines, phosphatidyl ethanolamines, and phosphatidyl inositols, glycolipids, such as cerebrosides and gangliosides, fatty diacylglycerides, glycosylglycerides, sphingolipids, and steroids, including sterols.

A "lipitoid" is a lipid-substituted peptoid, e.g. a compound of formula I above where Ra comprises a lipid moiety. A "cholesteroid" is a cholesterol-substituted peptoid, e.g. a compound of formula I above where $R^a$ comprises a cholesteryl moiety. While cholesterols are preferred, further disclosure of steroids useful for incorporating into steroid-peptoid conjugates is found in PCT publication WO 97/46223 (Fasbender et al.) and corresponding U.S. Pat. No. 5,935,936, which are hereby incorporated by reference. As used herein, the term "peptoid" encompasses lipitoids and cholesteroids.

One generally favored class of lipitoids includes compounds of the formula: L-linker-[N(CH$_2$CH$_2$NH$_2$)CH$_2$(C=O)—N(CH$_2$CH$_2$R)CH$_2$(C=O)—N(CH$_2$CH$_2$R)CH$_2$(C=O)]$_3$—NH$_2$, where the lipid group L is a fatty acid-derived group, such as a phospholipid group (i.e. ROOCCH$_2$CH(COOR)CH$_2$OP(O)$_2$O—), having fatty alkyl or alkenyl chains between about 8 and 24 carbon atoms in length, or a steroid-derived group, such as a cholesteryl group, and the portion of the molecule to the right of the linker is the peptoid segment. The linker may be a direct bond, or it may be a substantially linear linking group, such as an oligopeptide or an alkyl chain, of any effective length. The linker may also be an alkyl chain having one or more heteroatom-containing linkages, selected from the group consisting of ester, amide, carbonate, carbamate, disulfide, peptide, and ether, at either terminus of the chain or intervening between alkyl bonds. In selected embodiments, the linker is from 2 to about 30 atoms, or from 3 to about 15 atoms, in length. In the peptoid segment, R is selected from alkyl (branched or unbranched), aminoalkyl, and aralkyl. Aralkyl groups, such as benzyl or p-methoxyphenyl ethyl, are preferred. A single lipitoid may include different groups R, or they may be the same within the molecule.

Structures of useful peptoids are, or course, not limited to the class above, and may be easily varied by synthesis in the solid phase to produce libraries of compounds which may be screened by the methods described herein.

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Alkenyl" refers to an acyclic monovalent radical containing carbon and hydrogen, which may be branched or a straight chain, and which contains at least one carbon-carbon double bond. The alkenyl group may be monounsaturated or polyunsaturated. Similarly, "alkynyl" refers to such a radical having at least one carbon-carbon triple bond. "Lower" alkyl (alkenyl, alkynyl, alkoxy, etc.) refers to a group having 1 to 6 carbons, preferably 1 to 4 carbons.

"Aryl" refers to a substituted or unsubstituted monovalent aromatic radical having a single ring (e.g., benzene) or two or three condensed rings (e.g., naphthyl; phenanthryl). Groups having a single ring (monocyclic) or two condensed rings (bicyclic) are generally preferred, with monocyclic groups being particularly preferred. The term includes heteroaryl groups, which are aromatic ring groups having one or more nitrogen, oxygen, or sulfur atoms in the ring, such as furan, pyrrole, pyridine, imidazole, and indole. By "substituted" is meant that one or more ring hydrogens in the aryl group is replaced with a non-hydrogen group, preferably selected from halogen, lower alkyl, lower alkoxy, nitro, amide, tertiary amino, hydroxy, and halo(lower alkyl).

"Aralkyl" refers to an alkyl, preferably lower alkyl, substituent further substituted with an aryl group; e.g. benzyl. Similarly, "aralkenyl" and "aralkynyl" refer to alkenyl or alkynyl substituents further substituted with an aryl group.

An "oligonucleotide" employed in the screening methods of the invention is preferably between about 10 and 50, and more preferably between about 15 and 30, nucleotides in length.

Contacting a peptoid-oligonucleotide mixture "with a cell" includes contacting the mixture with a tissue containing such cells.

A "transfecting peptoid" is one which, in a given screening assay carried out in accordance with the invention, transfects the test cell or tissue with the test oligonucleotide.

"Physiologically relevant pH" is typically between about 5.5 and about 8.5; more typically between about 6.0 and about 8.0, and most typically between about 6.5 and about 7.5.

II. Oligonucleotide Transfection using Peptoid-Based Agents

Although many transfection agents exist for the delivery of plasmid DNA to cells in culture, less attention has been paid to the delivery of oligonucleotides. The present authors found that a series of peptoid-based transfection agents, previously characterized for transfection of plasmid DNA, were also able to form complexes with oligonucleotides and facilitated uptake of FITC-tagged oligonucleotides into many cell types, without significant cellular toxicity. Similar to results with transfection of DNA, transfection of oligonucleotides into cells was optimal at a +/− charge ratio of about 1.5-2/1, and the presence of serum did not have a negative influence at the ratios tested.

Figure 1B:
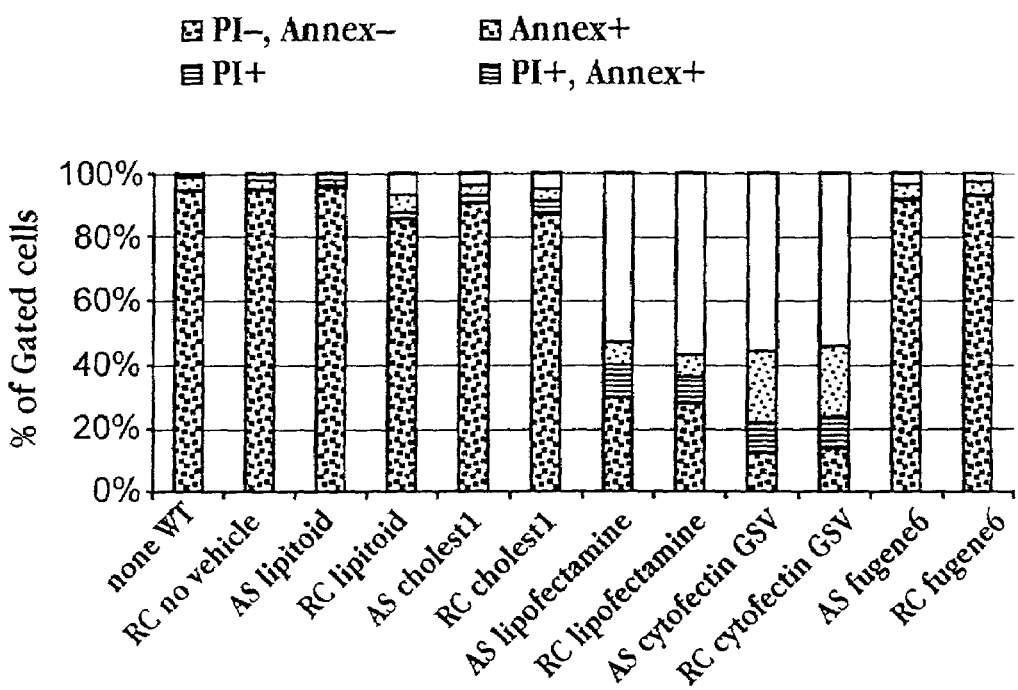
Figure 1C:
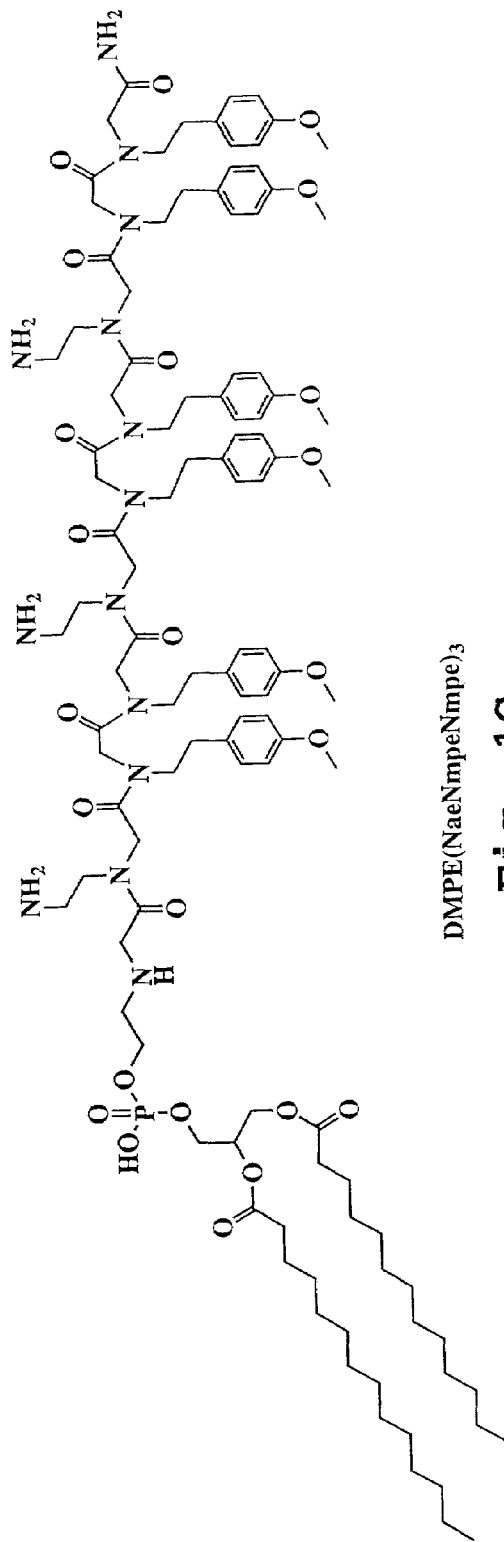
Figure 1D:
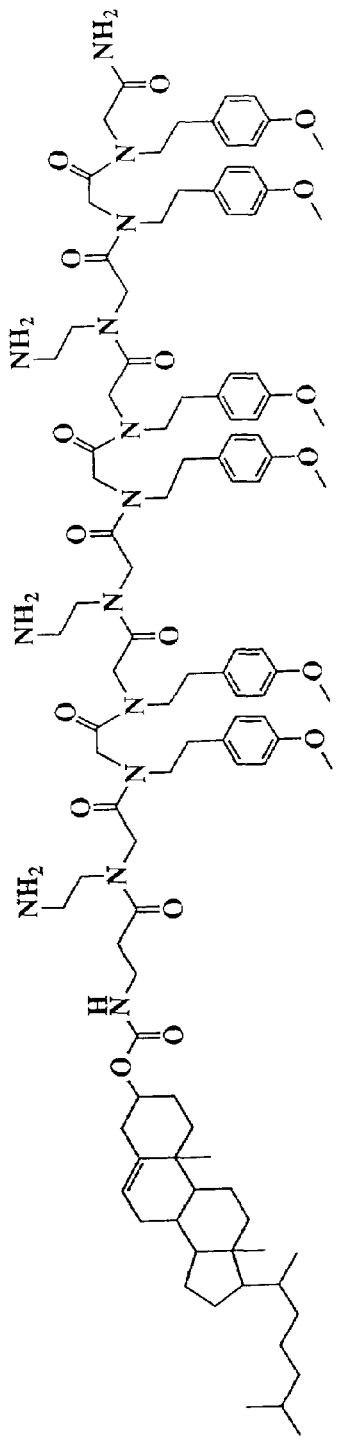

Lipid-cationic peptoid conjugates (lipitoids and cholesteroids, as described above) are particularly effective reagents for the delivery of plasmid DNA as well as oligonucleotides to cells. For example, FIGS. 1A-B show the transfection efficiency and toxicity of peptoid transfection agents (Lipitoid 1 and Cholesteroid 1; structures shown in FIGS. 1C-D, respectively) in comparison with commercially available transfection agents (Lipofectamine®, Cytofectin™ GSV, and FuGene™ 6) in transfection of SKOV3 (ovarian carcinoma) cells with 300 nM oligonucleotide. The oligonucleotide consisted of either 50 nM Akt1 antisense and 250 nM control oligonucleotide (AS) or 300 nM control oligonucleotide (RC=reverse control). Manufacturer's protocols were followed for the commercial transfecting agents. After overnight transfection, the cells underwent assays for production of RNA and quantitative real-time PCR analysis of Akt1 message levels.

The transfection data (FIG. 1A) shows that peptoid delivery vehicles were able to effectively deliver oligonucleotide into the cells. Akt1 message levels decreased >95% with Lipitoid 1 and >85% with Cholesteroid 1 compared to cells transfected with the matched reverse control. This level of knockout suggests that most cells were efficiently transfected with antisense oligonucleotide. This conclusion is supported by FACS analysis of SKOV3 cells transfected with a FITC-tagged oligonucleotide, in which >97% of cells were positive for FITC fluorescence (data not shown). In contrast, all the tested commercial agents either were ineffective in delivering the oligonucleotides (FuGene™ 6) or killed the cells (Lipofectamine®, Cytofectin™ GSV), as shown in FIG. 1B.

As a measure of cellular toxicity of the transfection agents, cells from the same transfections were stained with annexin V and PI, followed by FACS analysis (FIG. 1B). The fraction of cells positive for Annexin V, or for Annexin V and PI, are those in early or late stage apoptosis, respectively. Nontransfected control cells and cells transfected using Lipitoid 1, Cholesteroid 1, or Fugene™ 6 showed negligible staining with annexin V or PI. By contrast, cells transfected using Lipofectamine® or Cytofectin™ GSV were heavily stained with annexinV and PI, indicating that a high percentage of cells were undergoing programmed cell death.

III. Screening Method

In one aspect, the invention provides a method for screening a peptoid (which includes lipitoids and cholesteroids) for effectiveness in transfecting a cell with an oligonucleotide. The method includes the steps of: providing a plurality of different-sequence peptoids in separated compartments; forming a peptoid-oligonucleotide mixture in at least one of these compartments; contacting this mixture with a cell; and determining the degree of transfection of the cell by the oligonucleotide. The identity of the peptoid can then determined. While there is generally greater impetus toward identification of transfecting peptoids, identification of non-transfecting peptoids can also be useful.

Figure 2:
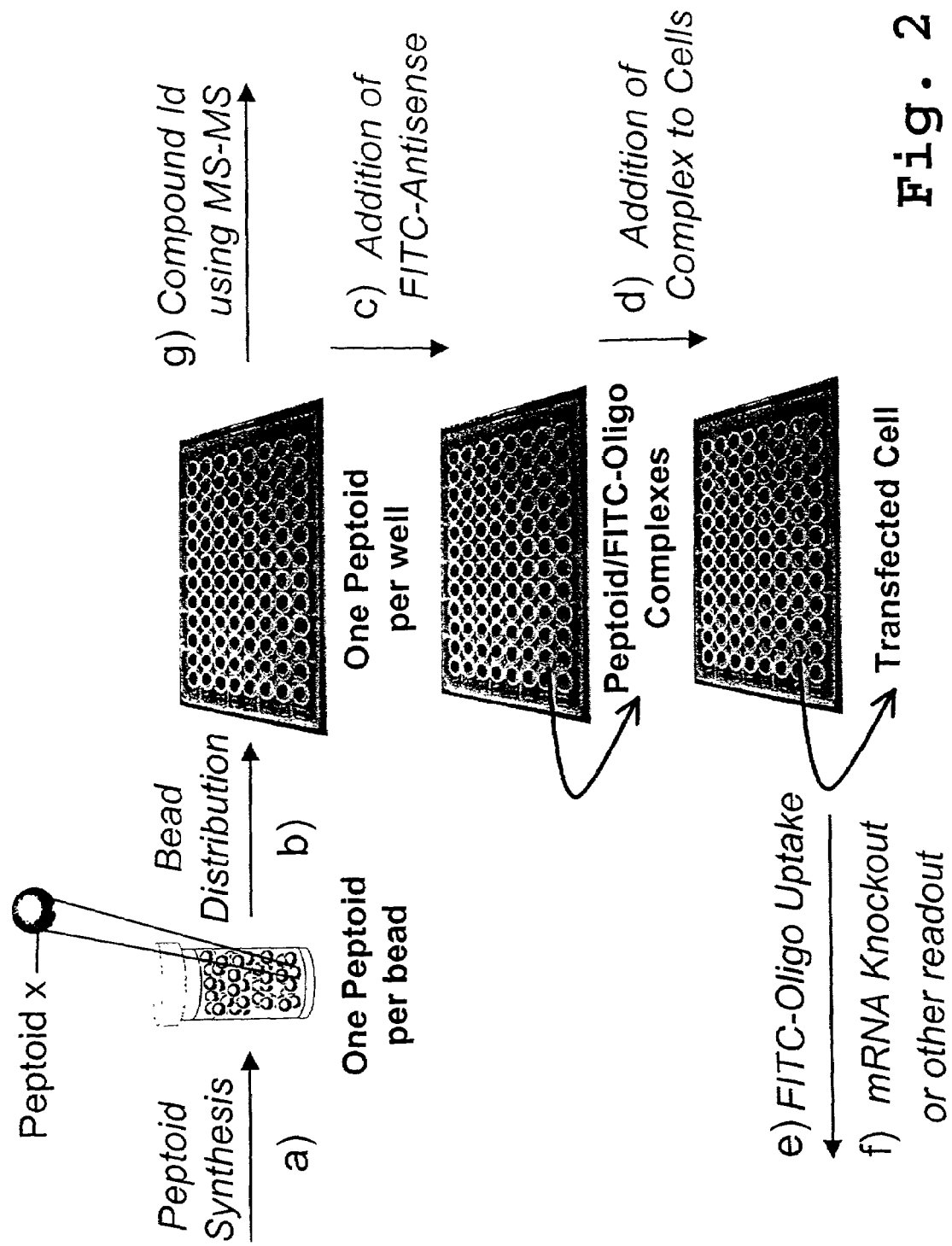
FIG. 2 is a flow diagram illustrating steps in screening a library of peptoid-based transfection agents for delivery of oligonucleotides.

FIG. 2 is a flow diagram illustrating steps in screening a library of peptoid-based transfection agents for delivery of oligonucleotides. The steps, to be described in more detail below, are as follows: a) A library of such compounds is synthesized, in one embodiment, by a mix-and-split protocol; b) a single bead, representing a single compound, is placed in each well of a multi-well plate, cleaved, and dissolved in water; c) each compound is used to form a complex with added oligonucleotide; d) each peptoid/oligonucleotide complex is added to cells in a similar multi-well format and tested for ability to transfect oligonucleotide into cells, as judged by multiple possible readouts, such as FITC-uptake (e) or loss of an antisense target message (f); the compound is then identified from the array of cleaved peptoids, using, in one embodiment, tandem mass spectrometry (MS-MS) (g).

A. Peptoid Synthesis

Peptoids, as defined above, are described in co-owned PCT Publications WO 94/06451, WO 98/06437, and WO 99/08711 (Zuckermann et al.), based on U.S. Ser. Nos. 60/023,867, 60/054,743, 07/950,853, and 09/132,808, which are hereby incorporated by reference. Preparation of peptoids by stepwise subunit addition is described in the above-referenced PCT Publications; see also Murphy et al., 1998 and Huang et al., 1998, and references therein. Briefly, an amine-derivatized solid phase support, preferably a "Rink amide" resin (4-(2',4'-dimethoxyphenyl-Fmoc-aminomethyl)-phenoxy resin; Nova Biochem) is bromoacetylated (following removal of the Fmoc group), and a primary amine having the first desired side chain is added, displacing the bromine. Further addition of bromoacetic acid (for a poly-NSG peptoid) and selected primary amines is alternated to construct the peptoid.

Preparation of peptoids is also discussed in Bartlett, Santi et al. 1991; Horwell, Pritchard et al. 1992; Haenel 1994; Zuckermann and Kerr 1994; Hadas and Hornik 1995; Desai, Nuss et al. 1996; Kobylecki and Gardner 1996; Ng, Warne et al. 1996; Zuckermann, Siegmund et al. 1998; Zuckermann, Troung et al. 1998; Zuckermann, Chinn et al. 1998; Zuckermann, Goff et al. 1999; 2000; and DE Utility Model Pubn. No. 20005738, all cited above, each of which is incorporated herein by reference in its entirety and for all purposes.

For preparation of lipitoids or cholesteroids, the N-terminus of a resin-bound peptoid is, preferably, first acylated with a spacer such as Fmoc-aminohexanoic acid or Fmoc-(β-alanine. After removal of the Fmoc group, the primary amino group is reacted with, e.g., cholesterol chloroformate, to form a carbamate linkage. A fatty acid-derived lipid moiety, such as a phospholipid, may be used in place of the steroid moiety. The steroid or other lipid moiety may also be linked to the peptoid moiety by other linkages, of any effective length, readily available to the skilled practitioner. The steroid or lipid moiety and peptoid segment can also be joined by a direct bond.

The plurality of different sequence peptoids is preferably a combinatorial library of peptoids. Such libraries can be prepared by applying known combinatorial synthesis strategies to the synthesis of peptoids, described further below. See, for example, Thompson et al., 1996; Terrett et al., 1995 and Bunin, 1998. In particular, particle-supported combinatorial libraries can be prepared containing a large number of polymers using the methods described in WO 99/58476 and corresponding U.S. patent application Ser. No. 60/084,843, which is incorporated herein by reference in its entirety and for all purposes.

Figure 3:
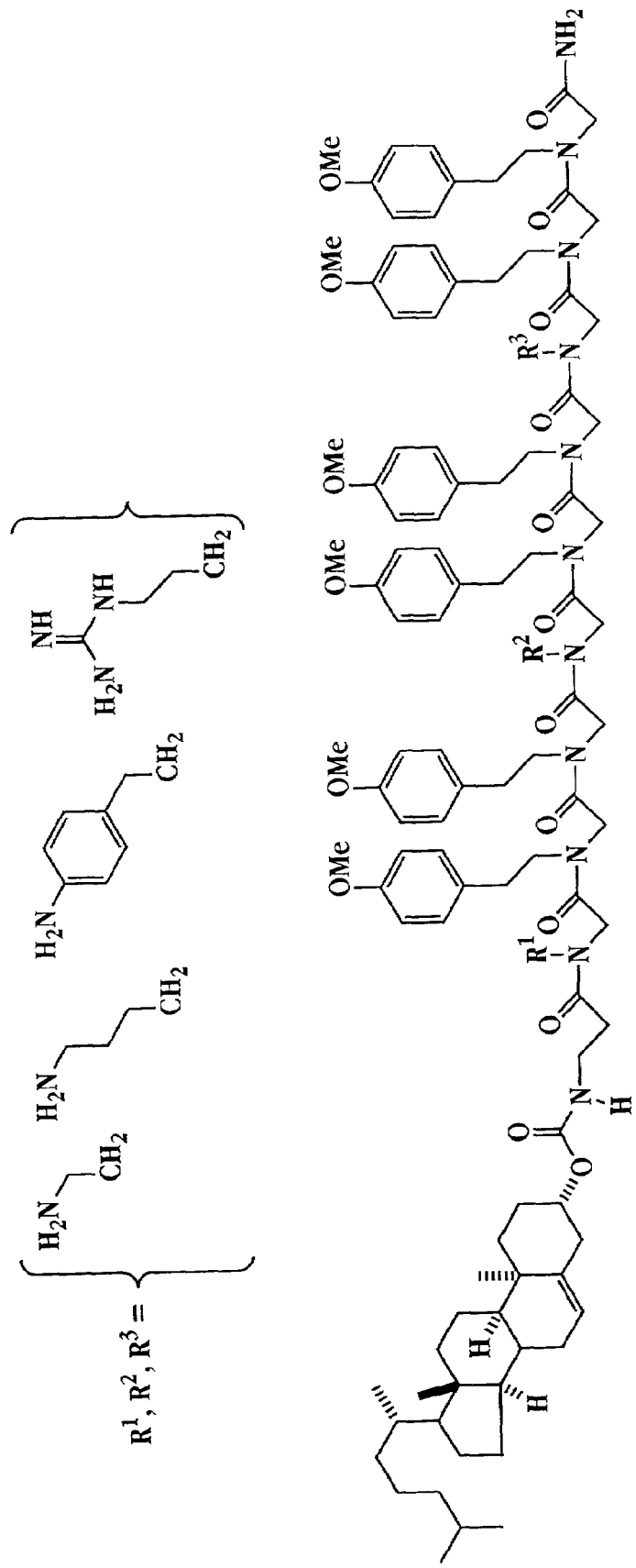
FIG. 3 shows a simple example of a peptoid (cholesteroid) combinatorial library.

Parameters varied in the synthesis of the peptoids include the N-side chains (incorporated by addition of primary amines) and the lipid terminal moiety. In one embodiment, the peptoids have a cholesteryl terminal moiety and different distributions of neutral and cationic N-side chains. A simple example of such a library is shown in FIG. 3.

The cationic character of the peptoid contributes to its interaction with the negatively charged oligonucleotides and eventually with the cellular phospholipids. Because the charge state can be modulated by the pKa of its basic functionalities and the local cellular pH, a set of peptoid basic side chains (pKa 4.5, 9 and 12, for an aniline, a primary amine and a guanidine group, respectively) with different lengths (ethyl, butyl, benzyl) were chosen as side chain substituents in the peptoid library. To explore the influence of a combination of these sidechains together, a basic functional group was incorporated at every third residue in a peptoid 9-mer, to evaluate 64 combinations. The other positions were occupied by a methoxyphenylethyl side chain, which has been found to give an appropriate balance of hydrophobicity (Huang, 1998; Murphy, 1998).

The different-sequence peptoids are most conveniently provided for screening on solid-phase supports, consistent with the solid phase syntheses generally employed for their preparation. A peptoid library, having one peptoid per bead, can be generated on polymeric beads by using a "mix and split" protocol, such as described above. It is preferable that the bead supports be high-loading beads (i.e. providing >1 nmole of compound per bead). It is also preferable that the bead supports have a substantially uniform diameter, such that the final reaction volumes of compounds cleaved from the bead supports will have substantially uniform compound concentrations.

For example, the library described above and shown in FIG. 3 was prepared using a mix-and-split synthesis protocol on polymeric beads (Furka, 1991; Lam, 1991; Zuckermann and Banville, 1992). An average loading of 40 nMol per bead (std dev ±10%) was observed, with 95% purity for a model compound.

In a typical procedure, such a pool of beads is swollen in a solvent such as dichloroethane and, if desired, sieved over a stainless steel mesh. The beads, each containing a single peptoid, are distributed, one bead per well, into an array of physically separated compartments, e.g. a 96-well plate, as shown in FIG. 2. This distribution can be accomplished using a bead distributor probe, as disclosed in WO 99/58476. Briefly, the bead distributor probe uses vacuum to select discrete beads from the mixture of beads and then uses a gas discharge to deliver the selected beads to a selected location, for example, into an array of wells.

The peptoids are released from the supporting beads by cleaving a cleavable linker between the peptoids and the beads. Many chemically cleavable linkages are known in the art; examples include disulfides (cleavable by reduction, typically using dithiothreitol), azo groups (cleavable with diothionate), sulfones (cleavable with basic phosphate, with or without dithiothreitol), glycols, cleavable by periodate, and esters, cleavable by hydrolysis. In the case of a Rink amide resin, as described above, or a Rink acid resin, cleavage from the resin is accomplished using trifluoroacetic acid (TFA), as described in the Examples, below. After cleavage, the cleavage mixture is removed by evaporation, and each peptoid is dissolved in water or aqueous buffer to obtain a library of different-sequence peptoid oligomer solutions, each typically having a concentration of about 0.5 mM.

In one embodiment, as discussed further below, a duplicate array of peptoid solutions is prepared by withdrawing aliquots of the respective peptoid solutions. This duplicate array is then used for later identification.

B. Transfection and Screening

An oligonucleotide whose transfection is to be screened is added to at least one compartment of the array of different-sequence peptoids. As noted above, the oligonucleotide is preferably between about 10 and 50, and more preferably between about 15 and 30, nucleotides in length. In a typical experiment, an oligonucleotide sample consists of two parts of an inactive (control, e.g. a reverse control) FITC-coupled oligonucleotide and one part of an active antisense oligonucleotide, e.g. an anti-Akt1 oligonucleotide. Conditions of addition are such that a transfecting peptoid forms a complex with the oligonucleotides. Suitable final concentrations of the components are about 200 nM oligonucleotide and 3 μM peptoid (see Examples).

Each peptoid-oligonucleotide mixture is then contacted with a cell, as in a cell culture or tissue sample. Cell cultures are typically prepared by plating at 10,000 to 30,000 per well on the day preceding transfection and, on the day of transfection, changing the contents of each well into 70 μL of fresh tissue culture medium containing serum. After overnight incubation, the cells are washed two times with fresh culture medium containing serum.

The cells are then screened for transfection of the oligonucleotide, according to methods known in the art. One such method comprises detecting a label, such as FITC, on the oligonucleotide. Cells that have taken up the oligonucleotide/peptoid complex can be identified, after washing, by scanning for FITC fluorescence using a fluorescent plate reader.

Alternatively, when the oligonucleotide is an antisense oligonucleotide, having a sequence directed against an portion of a DNA, pre-mRNA, or mRNA sequence which is involved in expression of a gene product in the cell, screening comprises detecting an alteration in the level of expression of the targeted gene in the cell. For example, mRNA is isolated from cells following transfection, a first-strand cDNA is prepared, and message levels for the test gene are measured, e.g. by real-time quantitative PCR.

These two methods can be combined by using a mixture of FITC-tagged control oligonucleotide and Akt1 antisense oligonucleotide, as described above. Transfected cells are first tested for FITC fluorescence, then lysed for isolation of RNA.

Figures 4A, 4B:
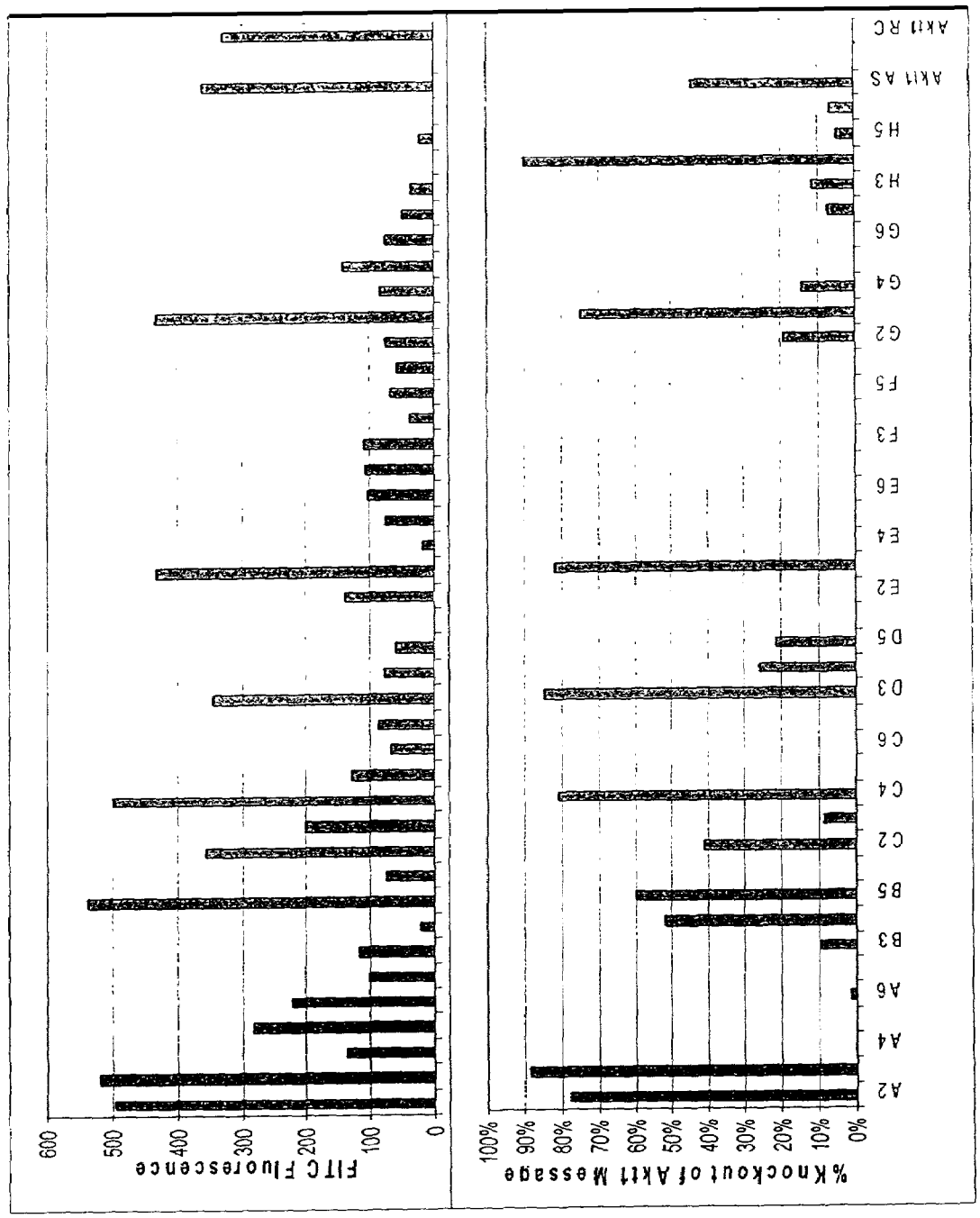
FIGS. 4A-B show the correlation between FITC-oligonucleotide uptake and loss of Akt1 message in MDA-MB-231 cells transfected with a mixture of FITC-oligonucleotide and Akt1-AS (antisense) oligonucleotide, using a library of combinatorial peptoids as delivery vehicles.

In one example, MDA-MB-231 cells were transfected with a mixture of FITC-oligonucleotide and Akt1-AS (antisense) oligonucleotide, using the above-described library of peptoids as delivery vehicles. FIGS. 4A-B show the correlation between FITC-oligonucleotide uptake and loss of Akt1 message in these cells. There is a good correlation between those samples showing good uptake of FITC-oligonucleotide and those showing loss of Akt1 message (as quantified by real-time quantitative PCR of first strand cDNA prepared from RNA from the cells), indicating that either FITC uptake or loss of targeted message could be used to identify active transfection agents.

It was observed that a small number of peptoids (e.g. in well H4) which apparently transfect Akt1-AS and cause loss of Akt1 message without an accompanying uptake in FITC-oligonucleotide. Thus, screening by FITC-uptake may miss a low percentage of peptoids which are capable of transfecting oligonucleotide into cells. For antisense oligonucleotides, compound selection is best based on data obtained from delivery of the oligonucleotide and the subsequent message knockout.

C. Compound Identification

Each transfecting peptoid, in each mixture contacted with cells shown to be transfected, can then be identified. As noted above, non-transfecting peptoids can also be identified, if desired. Preferably, this identification employs a replica of the mother plate, prepared, as described above, by transferring a small fraction of each well of the mother plate aqueous solution. In screening of multiple compounds, the well locations of the most efficient compounds are identified, and the identity of the peptoid responsible for transfection is determined, using the reserved solution from the mother plate.

Any method suitable for determining the sequences of peptoids can be used in accordance with this aspect of the present invention. In some embodiments, mass spectrographic methods are used. In one particular example, tandem mass spectrometry (MS-MS) has been found to be effective for characterizing the peptoid compounds described herein.

Figure 5A:
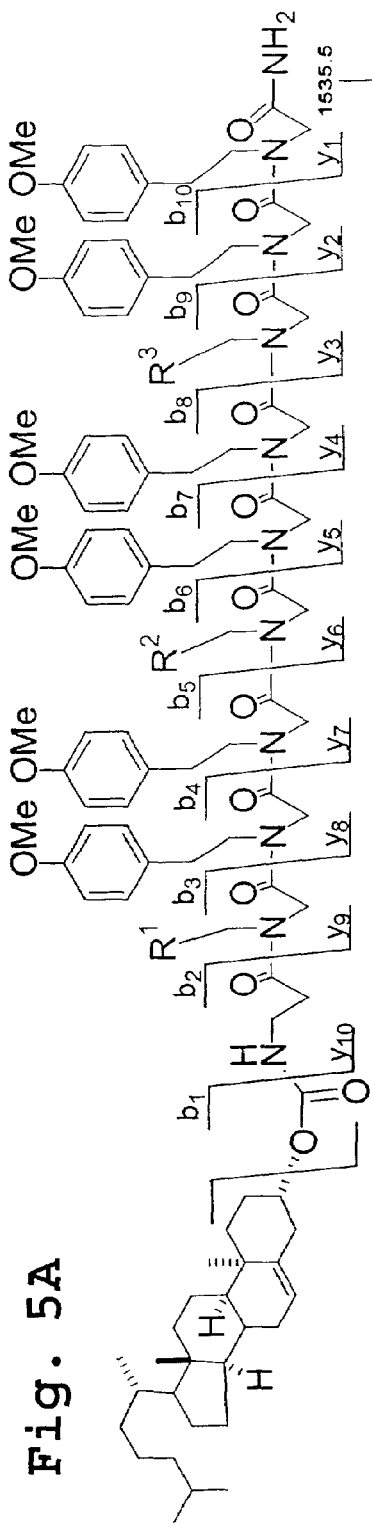
FIGS. 5A-B illustrates the identification of peptoid-based compounds, synthesized by a mix-and-split protocol, using nanospray MS/MS.
Figure 5B:
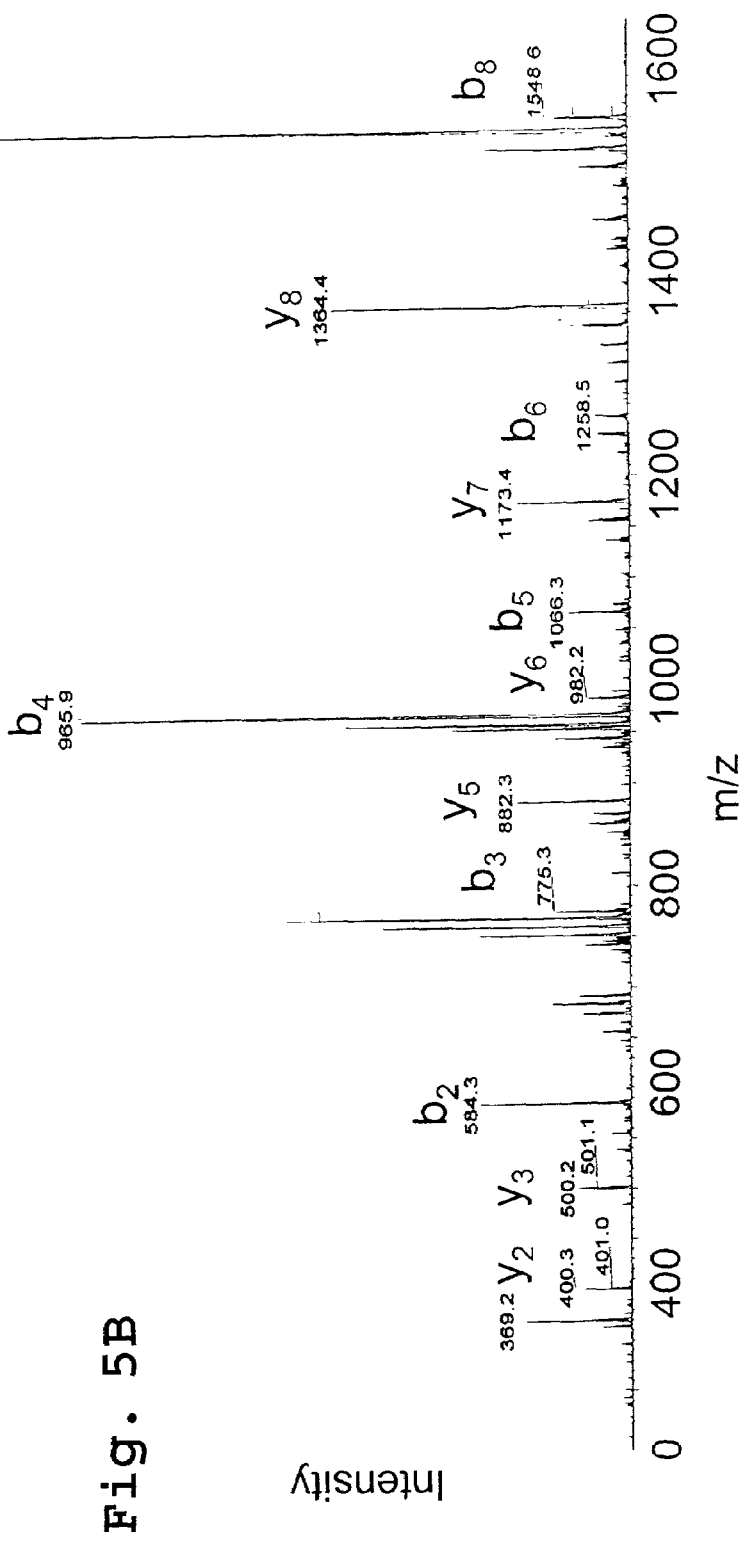

The sequences of peptoids that displayed interesting delivery profiles in the above-referenced Akt1 knockout assay were identified (FIG. 5) using nanospray tandem mass spectrometry (Smith, 1990; Carr, 1991). FIG. 5A shows the generic structure of a cholesteryl-peptoid conjugate, showing N-termninal fragments ("b-ions") and C-terminal fragments ("y-ions") expected to be generated by ionization in the mass spectrometer. FIG. 5B shows the spectrum of a representative cholesteryl-peptoid conjugate. Predicted fragments b2, b3, b4, b5, b6, b8, y2, y3, y5, y6, y7, and y8 were sufficient to unambiguously identify the sequence of this cholesteryl-peptoid conjugate.

Other MS-based methods of identification are also useful. For example, Edman degradation or partial capping during synthesis can be used to create a sequence ladder, followed by MS to determine the oligomer sequence.

Figure 6:
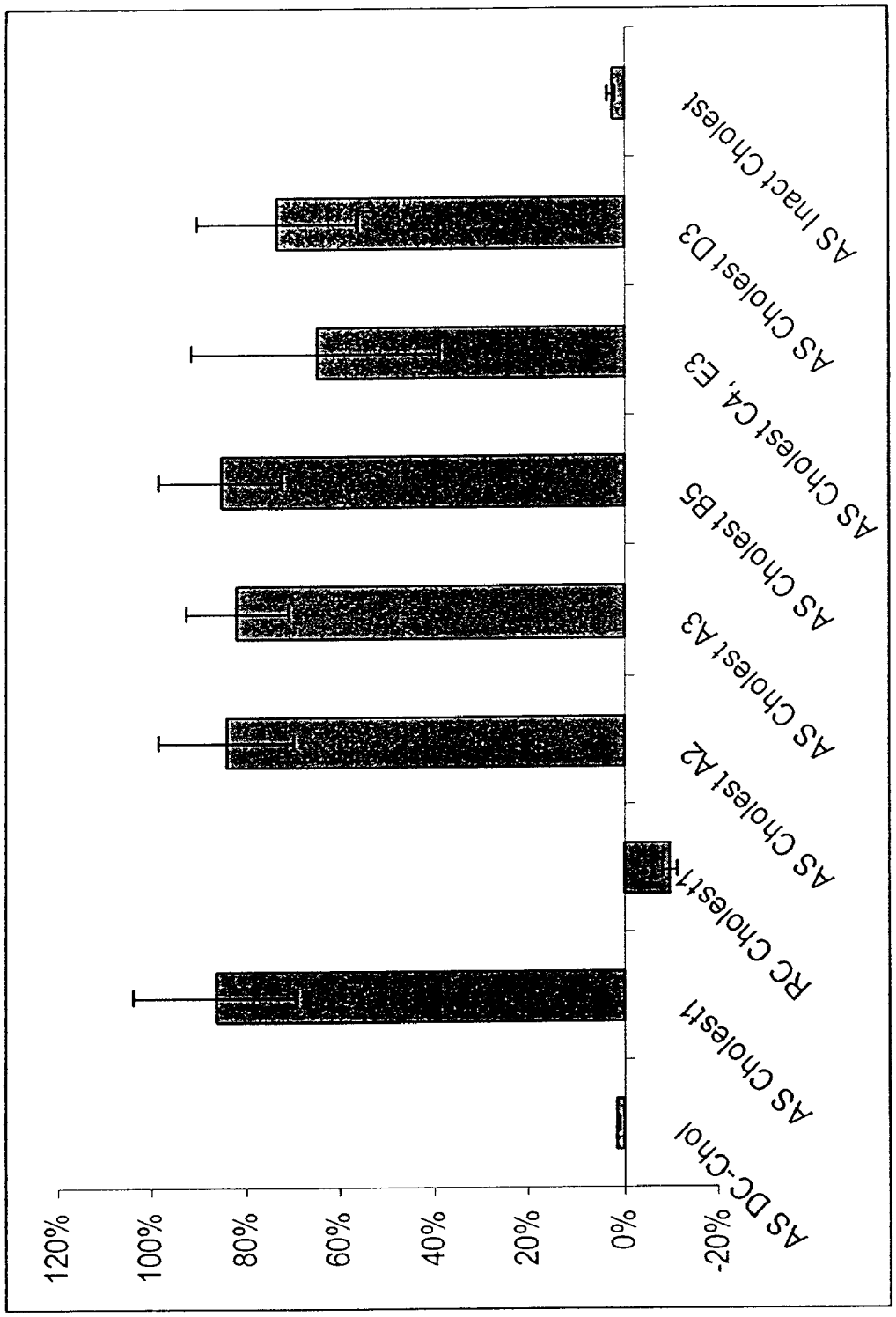
FIG. 6 shows message knockout by Akt-1 antisense transfected into MDA-231 cells using peptoids resynthesized following identification by MS/MS.
Figure 7A:
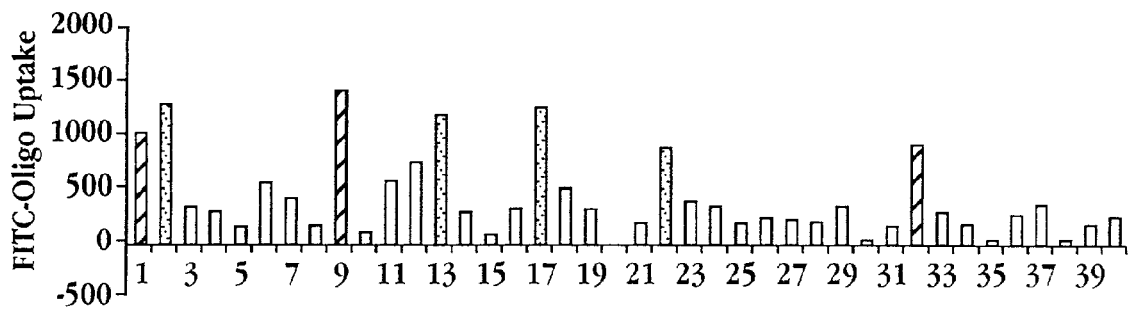
FIGS. 7A-D show transfection of four different cell lines (A: HCT 116 colorectal carcinoma cells; B: MDA-MB-231 breast adenocarcinoma cells; C: MCF7 breast adenocarcinoma cells; and D: human microvascular endothelial cells) using a library of combinatorially synthesized peptoid delivery vehicles.
Figure 7B:
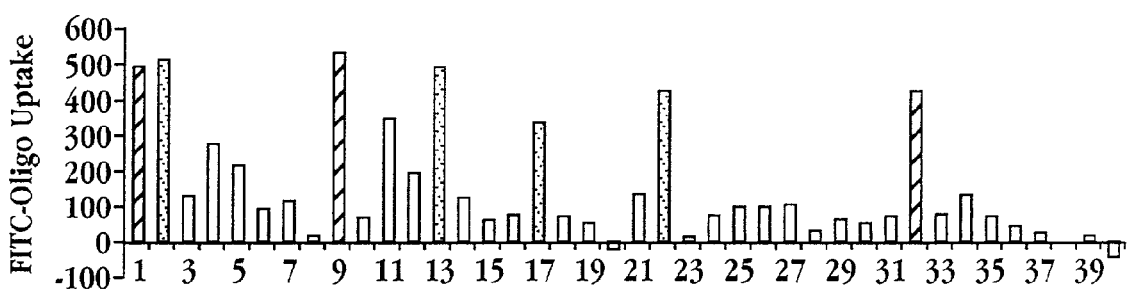
Figure 7C:
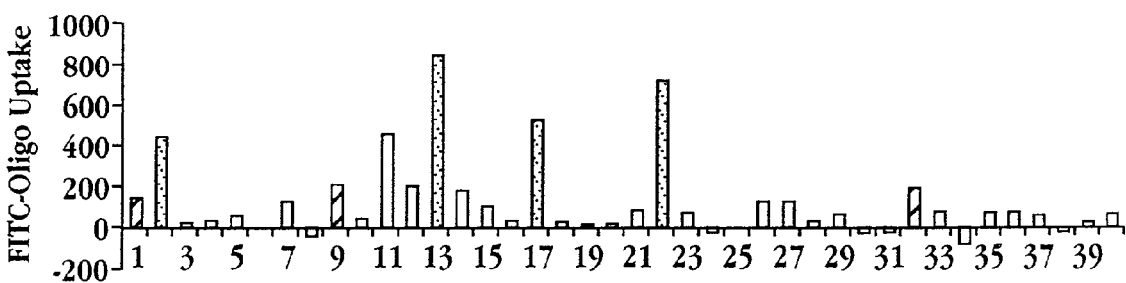
Figure 7D:
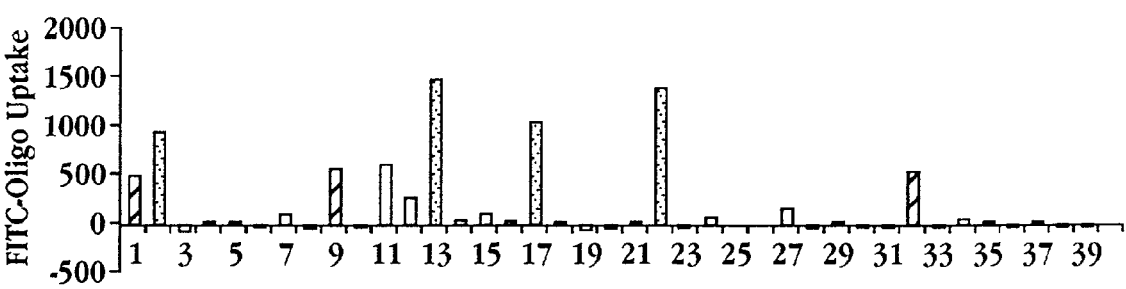
Figures 8A, 8B, 8C, 8D:
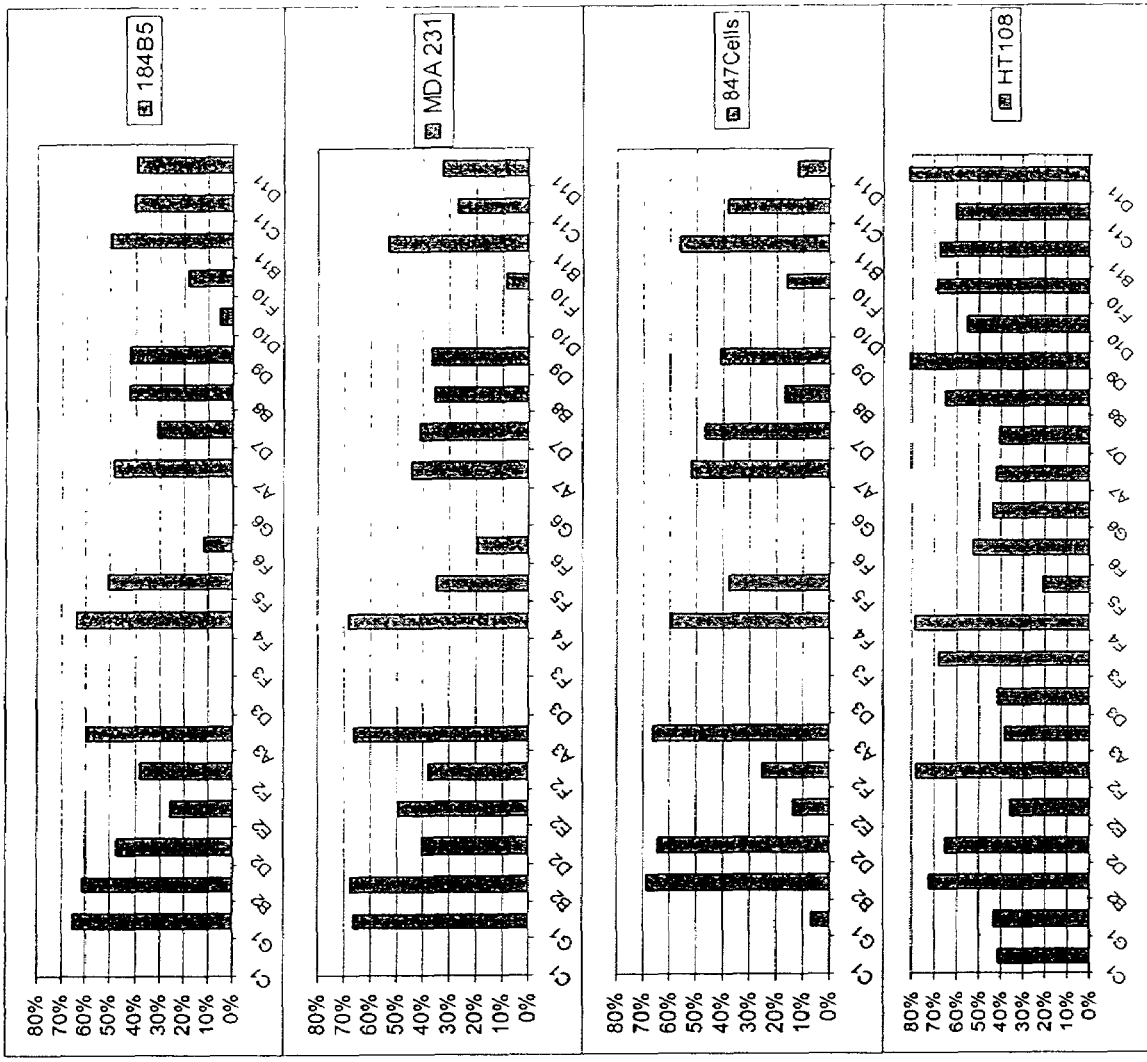
FIGS. 8A-D show transfection of four different cell lines (A. 184B5 breast epithelial cells. B. MDA-MB-231 breast adenocarcinoma cells. C. 847 fibroblast cells. D. HT1080 fibrosarcoma cells)using a library of combinatorially synthesized peptoid delivery vehicles.

Compounds which tested positive in wells A2, A3, B5, C4, D3, and E3 of FIG. 4 were resynthesized for confirmation of antisense oligonucleotide delivery (see FIG. 6). In the confirmation assay, MDA-MB-231 cells plated in 96-well dishes were transfected with a mixture of 200 nM FITC-oligo and Akt1-AS (antisense) or Akt1-RC (reverse control) oligo, using a variety of cholesteroid or cholesterol delivery vehicles. Five of these were novel cholesteroids selected as active transfection agents according to the method of the invention and resynthesized following identification by MS/MS. One of these cholesteroids, designated "Inact Cholest", is a novel cholesteroid that was negative for oligonucleotide delivery in the initial screening. Cholesteroid 1 (see FIG. 1) was used as a positive control delivery vehicle, and DC-cholesterol as a negative control. After overnight transfection, RNA was isolated from the cells, and quantitative real-time PCR was used to determine Akt1 and actin message levels. Each bar in FIG. 6 represents percentage knockout in Akt1 message relative to actin message when compared to nontransfected cells. Error bars represent standard deviation among the four wells transfected using each delivery vehicle.

As shown in FIG. 6, the resynthesized cholesteroids gave efficient knockout of Akt1 message in MDA-23 1 cells. Thus the protocol for synthesis and identification of novel transfection agents was shown to isolate compounds that retain their favorable characteristics upon resynthesis.

D. Screening for Selective Transfection

In one embodiment of the method, the cells or tissue used for transfection comprise (in separate compartments, or separate arrays) distinct cell types. The screening method is thus used to identify peptoids capable of selectively delivering oligonucleotides to a selected cell type relative to a non-selected cell type. For example, the selected cell type may be a tumor cell, while the non-selected cell type is a non-tumor cell. In another example, the selected cell type is an endothelial cell, and the non-selected cell type is an epithelial cell. In such applications, more than one duplicate array of peptoids could be generated, with one reserved for identification purposes and each of the others used for screening of transfection of a given cell or tissue type. This procedure can be used to screen for delivery vehicles that selectively transfect a given tissue, e.g. as an aid to gene therapy in animals.

One example of differential cell screening is shown in FIGS. 7A-D. Four different cell lines, including three tumor cell lines (A: HCT116 colorectal carcinoma cells; B: MDA-MB-231 breast adenocarcinoma cells; C: MCF7 breast adenocarcinoma cells) and one non-tumor cell line (D: human microvascular endothelial cells), were transfected using a library of combinatorially synthesized peptoid delivery vehicles. Cells were transfected with 200 nM Akt1-AS oligonucleotide and control-FITC oligonucleotide and delivery vehicle, as described in the Examples, and oligonucleotide uptake was quantified by cell fluorescence after overnight transfection. In the Figures, stippled bars indicate compounds that were effective in all cell types, while hatched bars represent compounds effective only in cell types having metastatic potential. As shown in the Figures, three of the compounds fall into the latter category.

A further example is shown in FIGS. 8A-D. Four cell types were transfected, using a single panel of peptoid-based compounds to deliver a FITC-control oligonucleotide/Akt1 antisense oligonucleotide mixture. Breast epithelial 184B5 cells and 847 fibroblasts are non-tumor forming cells, whereas MDA-MB-231 breast adenocarcinoma cells and HT1080 fibrosarcoma cells are tumor forming and metastatic cell types. Some of the tested compounds were able to cause increased transfection of all four cell types, as indicated by knockout of Akt1 message (e.g. compounds from wells B2 and F4). Other compounds promoted Akt1 knockout in some, but not all, of the four cell types (e.g. compounds from well C1, F5, G6, D10, and D11).

Such screening is useful in identification of compounds that selectively transfect oligonucleotides in cells that are selected for some particular characteristic. Such selectivity in transfection would be particularly useful for delivery of antisense oligonucleotides in vivo.

The peptoid-based agents described herein are effective oligonucleotide transfection agents, providing a high transfection efficiency, effective loss of test message in response to antisense oligonucleotide, low toxicity, and compatibility with serum. By using combinatorial synthesis on beads, preferably in combination with an automated bead-picking procedure, a large number of novel peptoid conjugates can be generated in quantity and purity suitable to be used directly in a high throughput screen, e.g. an mRNA knockout screen, in a variety of cell lines.

One of the characteristics of these peptoid-based transfection agents that makes it feasible to screen them for transfection in such a format is that they do not require formulation with other lipids. However, once a peptoid is identified as effective in transfecting oligonucleotide into a particular cell type, it may be possible to modify or enhance these characteristics by formulation with other lipids.

EXAMPLES

The following examples illustrate but are not intended to limit the invention.

Peptoid Synthesis. Solvents, amines, and other reagents were purchased from commercial sources and used without further purification. Peptoid oligomers were synthesized on 50 µmol of Rink amide resin (Nova Biochem) by a modification of previous methods (Zuckermann, Kerr et al., 1992; Figliozzi, 1996). After removal of the first Fmoc group, the following monomer addition cycle was performed by a robotic synthesizer and repeated until the desired length was obtained.

The amino-resin was bromoacetylated by adding 830 µl of 1.2 M bromoacetic acid in N,N-dimethylformamide (DMF) and 200 µl of N,N'-diisopropylcarbodiimide (DIC). This solution was agitated for 40 min at 35° C., drained, and washed with DMF (3×2 ml). Next, 0.85 ml of a 1 M solution of a primary amine in DMSO was added, to introduce the side chain. This solution was agitated for 40 min at 35° C., drained, and washed with DMF (4×2 ml). In an alternative procedure, amines were dissolved in N-methylpyrrolidone instead of dimethylsulfoxide.

Peptoids were released from the beads using TFA 50% (v/v) in dichloroethane with 1% triethylsilane. Each macrobead was picked using a automated bead picker (PCT Pubn. No. WO 9958476) and transferred to polypropylene 96 well plates (V-form, Greiner) to be cleaved and stored.

Conjugation with Cholesterol. A peptoid-cholesterol conjugate (cholesteroid) was prepared as follows. The amino terminus of a resin-bound peptoid was treated with FMOC-β-Ala-OH (0.24 eq) and DIC (0.26 eq) in DMF for 20 min at 85° C. The support was washed with 3×2 ml DMF. Piperidine (20% v/v in DMF, 3 ml) was added, followed by 20 eq cholesteryl chloroformate and 20 eq DIEA (neat, 173 µl). Following completion of the reaction, the conjugate was cleaved from the support by treatment with 50% (v/v) TFA in $CH_2Cl_2$.

Combinatorial Synthesis (Mix-Split) Protocol. The following illustrative mix-split protocol was used for a combinatorial synthesis of sixty-four different-sequence peptoids, employing four different primary amines. Each "submonomer cycle" comprised bromoacetylation followed by addition of a primary amine.

Resin Fmoc deprotection
DMF wash
Submonomer cycle 1
Submonomer cycle 2
Distribute resin to 4 vessels,
Drain reaction vessels
Submonomer cycle 3
Recombine resin into single vessel,
Drain reaction vessels
Submonomer cycle 4
Submonomer cycle 5
Distribute resin to 4 vessels,
Drain reaction vessels
Submonomer cycle 6
Recombine resin into single vessel,
Drain reaction vessels
Submonomer cycle 7
Submonomer cycle 8
Distribute resin to 4 vessels,
Drain reaction vessels
Submonomer cycle 9
Fmoc-(-Ala coupling
Chloroformate coupling (formation of lipid or cholesteryl conjugate)

Cleavage of Library Compounds from Bead Supports. A cleavage cocktail (TFA/DCE, 50:50, 75 µL) was added to each bead-containing well in a multiwell plate. After an hour, the plate was transferred to a speed-vac evaporator (evaporator Savant AES200 equipped with a 96-well plate carrier rotor) to remove most of the volatiles from the plate. Each well was treated with acetonitrile/water solution ($CH_3CN$ 50% [v/v] in $H_2O$, 75 µL) and agitated for 10 min using a microtiter plate shaker. The plate was transferred to the speed-vac evaporator and the volatiles removed for a 30 minute period. The contents of each well (typically a single peptoid compound) were dissolved in water or buffer (80 µL), transferred to a polypropylene 96-well plate (200 µL, v-shaped bottom), and stored, if necessary, at −20° C.

Transfection. For transfections in 6-well dishes, cells were plated at 250,000 cells per well one day before transfection to yield a density of 60-80% at transfection. Antisense or reverse control oligonucleotide was diluted to 2 µM in Opti-MEM (Invitrogen Life Technologies, Carlsbad, Calif.) for transfection. Peptoid transfection agents were diluted to a ratio of 1.5 nmol vehicle per µg oligonucleotide in the same volume of Opti-MEM. The diluted oligonucleotide and the diluted peptoid vehicle were then mixed and immediately added to cells in culture medium to a final concentration of 200-300 nM oligonucleotide as indicated for each experiment. After overnight incubation, the transfection mixture was replaced with fresh culture medium.

Transfections were similar for 96-well screening and retesting of vehicles except that cells were seeded at 20,000 per well and all mixing and dilution steps were performed using a Sagian Multipette 96-channel Pipettor. Cells to be screened were plated at 10,000 to 30,000 per well in two 96-well tissue culture dishes on the day before the transfection. On the day of the transfection, the cells were changed into 70 µl of fresh tissue culture medium containing serum. Oligonucleotide, consisting of 2 parts of an inactive FITC-coupled oligonucleotide and one part antisense oligonucleotide, was diluted in Opti-MEM to 1.3 µM. Peptoid compounds to be tested for delivery of oligonucleotides were arrayed in 96-well format at 0.5 mM concentration in water. Two microliters of each was diluted into Opti-MEM to a concentration of 20 µM. Diluted oligonucleotides were mixed into diluted peptoids, and the peptoid-oligonucleotides formed were further diluted onto the cells in medium. Duplicate plates of cells were transfected with a final concentration of 200 nM oligonucleotide and 3 μM peptoid. After overnight transfection, the cells were washed two times with medium containing serum.

For comparison of commercial transfection agents with peptoid transfection agents, Lipofectamine (Invitrogen Life Technologies), Cytofectin GSV (Glen Research, Sterling, Va.), and Fugene 6 (Roche Molecular Biochemicals, Indianapolis, Ind.) were used according to package directions and cells were transfected overnight in Opti-MEM (Lipofectamine and Cytofectin GSV) or medium with serum (Fugene 6).

Antisense oligonucleotides were synthesized at Chiron Corporation according to standard methods and had the following sequences:
AKT1-AS: CCATAGTGAGGTTGCATCTGGTGCC (SEQ ID NO: 1);
AKT1-RC: CCGTGGTCTACGTTGGAGTGATACC (SEQ ID NO: 2).

RNA Isolation and PCR. RNA from cells transfected in 6-well format was isolated using the High Pure RNA Isolation Kit (Roche Diagnostics Corporation, Indianapolis, Ind.). For cells transfected in 96-well format, the RNeasy 96 Kit (Qiagen, Valencia, Calif.) was used. RNA was reverse transcribed using MMLV reverse transcriptase and RNasin (Ambion) and oligo-d(T)18 synthesized at Chiron Corporation. A 2 μl aliquot of each 20 μl RT reaction was quantified for Akt1 or actin message levels using a Gene Amp 5700 and Sybr Green PCR Master Mix from Applied Biosystems (Foster City, Calif.). The resulting quantities for Akt1 message level were normalized to actin message levels from the same sample to normalize for variations in RNA yield or reverse transcription.

Primers used for quantitative PCR were synthesized at Chiron Corporation according to standard methods, and had the following sequences. Primers were used at a final concentration of 180 nM.
β-actin forward: 5'-CGGGAAATCGTGCGTGACAT-TAAG-3'(SEQ ID NO: 3);
β-actin reverse: 5'-TGATCTCCTTCTGCATCCTGTCGG-3' (SEQ ID NO: 4);
Akt1 forward: 5'-GAAGTGGGGCCTGCGCTCGCTGT-3' (SEQ ID NO: 5);
Akt1 reverse: 5'-ATCGTGTGGCAGCACGTGTACG-3' (SEQ ID NO: 6).

Tandem Mass Spectrometry. For deconvolution, each peptoid solution plate was dried in a speed-vac evaporator Savant AES200 for 60 min, and a solution of $CH_3CN$ in $H_2O$ (100 μl) was added to each well. The resulting solution was used for MS-MS analysis. In some cases, a C4 ZipTip purification step was performed, according to the manufacturer's instructions.

Apoptosis Assay. Following transfection with antisense oligonucleotides and various transfection agents, cells were gently removed from plates using 0.05% trypsin and 2 mM EDTA, washed in a buffer containing 10 mM Hepes pH7.2, 140 mM NaCl, 5 mM $CaCl_2$, and stained with Propidium iodide at a final concentration of 1 μg/ml and Annexin-V-FLUOS (Roche Molecular Biochemicals). Cells were then analyzed for staining with each marker using a Becton Dickinson FACScan.

While the invention has been described with reference to specific methods and embodiments, it will be appreciated that various modifications may be made without departing from the invention.

It is claimed:

1. A method of identifying peptoids which are effective in transfecting a cell with an oligonucleotide, the method comprising (i) providing a library of peptoids in an array of physically separated compartments, said peptoids having a plurality of different sequences and having the general formula I:

$$R^a-(N-CR^1R^2-C)_m-R^c$$
$$\quad\quad |\quad\quad\quad ||$$
$$\quad\quad R^b\quad\quad\ \ O$$

where $R^a$ is selected from the group consisting of alkyl, aryl, aralkyl, aralkenyl, and aralkynyl, any of which may be substituted with one or more groups X hydrogen, —OH, —SH, —COOH, sulfonyl, and a lipid moiety, wherein said lipid moiety may be conjugated to a linker moiety, each $R^b$ is independently selected from the group consisting of alkyl, aryl, aralkyl, aralkenyl, and aralkynyl, any of which may be substituted with one or more groups X; and hydrogen, wherein at least one group $R^b$ is not hydrogen;

$R^c$ is selected from the group consisting of alkyl, aryl, aralkyl, aralkenyl, and aralkynyl, any of which may be substituted one or more groups X; hydrogen, —OH, —SH, —NH$_2$, —NHR, —NH(C=O)R, where R is lower alkyl; sulfonyl, hydrazine, and a lipid moiety, wherein said lipid moiety may be conjugated to a linker moiety;

X is selected from hydroxy, alkoxy, amino, guanidino, amidino, alkylamino, alkylthio, halogen, nitro, cyano, keto, aldehyde, carboxylic acid, carboxylic ester, carboxylic amide, sulfonic acid and sulfonic ester;

at least one of $R^a$ and $R^c$ comprises a lipid moiety;

$R^1$ and $R^2$ are independently selected from hydrogen, lower alkyl, and lower alkoxy; and m is an integer selected from 2 to about 50, wherein the sequences of individual peptoids in the library are unidentified;

(ii) contacting a plurality of peptoids having unidentified sequences from the library provided in (i) with an oligonucleotide, to form a plurality of peptoid-oligonucleotide mixtures, wherein said oligonucleotide is between about 10 and 50 nucleotides in length, and is a fluorescently labelled or an antisense oligonucleotide, and wherein said contacting is performed in an array of physically separated compartments;

(iii) contacting each said mixture with a cell in an array of physically separated compartments;

(iv) screening each cell for transfection of the oligonucleotide, to identify transfected cells; and (v) identifying transfecting peptoids in mixtures contacted with transfected cells.

2. The method of claim 1, wherein said peptoids are supported on beads in said physically separated compartments.

3. The method of claim 2, wherein each compartment contains a single beads, and each beads contains a single peptoid.

4. The method of claim 1, wherein, in step (iii), each said mixture is contacted with a plurality of distinct cell types.

5. The method of claim 1, wherein in formula I, $R^a$ comprises a lipid moiety, and $R^e$ is selected from $-NH_2$, $-NHR$, and $-NH(C=O)R$, where R is lower alkyl.

6. The method of claim 5, wherein said lipid moiety is a sterol.

7. The method of claim 1, wherein in formula I, each of $R^1$ and $R^2$ is hydrogen.

8. The method of claim 1, wherein providing said library comprises synthesizing the library by a mix-and-split protocol.

9. The method of claim 1, wherein identifying transfecting peptoids comprises determining their sequence.

10. The method of claim 9, wherein the peptoid sequence is determined by tandem mass spectrometry.

* * * * *

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1
ccatagtgag gttgcatctg gtgcc                                           25

<210> SEQ ID NO 2
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 2
ccgtggtcta cgttggagtg atacc                                           25

<210> SEQ ID NO 3
<211> LENGTH: 24
<212> TYPE: DNA
<213> ORGANISM: Artificial Sequence
<220> FEATURE:
<223> OTHER INFORMATION: primer

```
<400> SEQUENCE: 3
cgggaaatcg tgcgtgacat taag                                              24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
tgatctcctt ctgcatcctg tcgg                                              24

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gaagtggggc ctgcgctcgc tgt                                               23

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
atcgtgtggc agcacgtgta cg                                                22
```